United States Patent [19]

Yardley

[11] 4,021,560
[45] May 3, 1977

[54] 2-[(DIMETHYLAMINO)(3-PYRIDYL)METHYL]CYCLOHEXANOL AND RELATED COMPOUNDS

[75] Inventor: John P. Yardley, King of Prussia, Pa.

[73] Assignee: American Home Products Corporation, New York, N.Y.

[22] Filed: Aug. 11, 1975

[21] Appl. No.: 603,552

[52] U.S. Cl. .......................... 424/263; 260/295 R; 260/296 R
[51] Int. Cl.² ...................................... C07D 213/38
[58] Field of Search ............... 424/263; 260/295 R, 260/296 R

[56] References Cited

UNITED STATES PATENTS

| | | | |
|---|---|---|---|
| 3,396,224 | 8/1968 | Van Heyningen | 424/263 |
| 3,849,423 | 11/1974 | Krumkalns et al. | 260/294.86 |

*Primary Examiner*—Cecilia Jaisle
*Attorney, Agent, or Firm*—Robert Wiser

[57] ABSTRACT

2-[(Dimethylamino)(3-pyridyl)methyl]-cyclohexanol and related compounds, methods for their preparation and use are disclosed. The final products have analgesic activity.

10 Claims, No Drawings

2-[(DIMETHYLAMINO)(3-PYRIDYL)METHYL]-CYCLOHEXANOL AND RELATED COMPOUNDS

BACKGROUND OF THE INVENTION

In U.S. Pat. No. 2,767,185, a process is described for the preparation of certain amino cycloanol compounds of the formula:

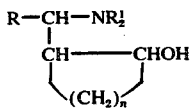

wherein $n$ is an integer from 3 to 5, R is a phenyl radical and $NR_2^1$ is a secondary amino group selected from the class consisting of the N-methyl-N-alkylamino and N-methyl-N-aralkylamino radicals, piperidino, morpholino pyrrolidino and N'-alkylpiperazino radicals. These compounds are produced by the reaction of benzalcyclanones with appropriate secondary amines followed by reduction. The specific utility ascribed to the products in this patent was the use of the N'-alkylpiperazine compounds as intermediates in the preparation of corresponding hexahydro-benzhydryl piperazines whose quaternary salts are stated to be powerful spasmolytics. This utility is further described in U.S. Pat. No. 2,748,126.

In Baltzly et al., J. A. C. S., 77, 624 (1955), the reaction of secondary amines with benzalcyclanones followed by reduction to afford aminocycloanols is further described.

Huisgen et al., Chem. Ber., 101, 2043 (1968) described the addition of C-phenyl nitrone to cyclopentene or cyclohexene to give a corresponding isoxazolidine and in the case of the cyclopentene, reduction to afford an α-methylamino-benzylcyclopentanol.

Belgian Pat. No. 797,827, Oct. 5, 1973, discloses benzylamine cycloanol analgesics.

The present invention deals with 2-[(dimethylamino)(3-pyridyl)methyl]cyclohexanol and compounds closely related thereto which have been found to have an analgesic activity.

SUMMARY OF THE INVENTION

The invention sought to be patented in a first composition aspect of the invention resides in the concept of a compound of the formula:

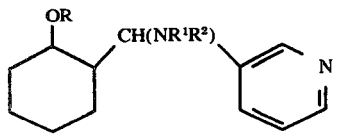

wherein R is hydrogen, lower alkyl, or lower alkanoyl; $R^1$ is methyl; and $R^2$ is methyl, ethyl, or benzyl; and the pharmacologically acceptable acid addition salts thereof.

The tangible embodiments of the principal composition aspect of the invention possess the inherent general physical properties in the free base form of being colorless to yellow oils, or solids, substantially insoluble in water, and generally soluble in organic solvents such as ether, benzene, hexane, acetone and pyridine. In the form of their acid addition salts they are generally white or off-white crystalline solids, appreciably soluble in water. Examination of the compounds produced according to the hereinafter described process reveals, upon infrared, ultraviolet, and nuclear magnetic resonance spectrographic analysis, spectral data supporting the molecular structure hereinbefore set forth. The aforementioned physical characteristics, taken together with the nature of the starting materials, the elemental analysis, and the products obtained therefrom, further confirm the molecular structure hereinbefore set forth.

The invention sought to be patented in its process aspect resides in the concept of a method for producing analgesia in warm-blooded animals which comprises administering to a warm-blooded animal in need thereof an amount sufficient to produce analgesia in said warm-blooded animal of a compound of Formula I.

The invention sought to be patented in its second composition aspect resides in the concept of a composition suitable for administration to a warm-blooded animal comprising:
a. a compound of Formula I; and
b. a pharmaceutically acceptable carrier.

DESCRIPTION OF THE PREFERRED EMBODIMENTS

The starting material for the synthesis of the compounds of Formula I, namely 2-(3-pyridylmethylene)-cyclohexanone (II) is known in the literature. J. Sam and K. Aparajithan, J. Pharm. Sci., 56, 644 (1967) describe the compound, preparing it by the reaction of 3-pyridine aldehyde with the morpholine eneamine of cyclohexanone.

Treatment of II with the appropriate secondary amine, such as dimethylamine, N-methyl-ethylamine, or N-methyl-benzylamine, at moderate temperatures, conveniently room temperature, either with or without an inert solvent, for a period of time sufficient to allow a practical amount of conversion to occur, conveniently about 24 to about 48 hours, gives the corresponding 2-[(disubstituted amino)(3-pyridyl)methyl]-cyclohexanone (III). The product may, if desired, be used for further synthesis without treatment other than removal of unreacted amine. For example, if 2-(3-pyridylmethylene)cyclohexanone is treated with dimethylamine at room temperature, conveniently in a pressure bottle, as the boiling point of dimethylamine is less than room temperature, for about 36 hours, 2-[(dimethylamino)(3-pyridyl)methyl]cyclohexanone (IIIa) is obtained from which the more volatile dimethylamine may be removed by evaporation in vacuo. Treatment of III with a carbonyl reducing agent such as THF-borane in an inert solvent, conveniently tetrahydrofuran (THF), initially at reduced temperature, conveniently about 0° to about 10° C., then at moderate temperature, conveniently ambient temperature, followed by work-up by standard techniques, conveniently decomposing the reaction complex with water initially at reduced temperature, typically at about 5° C., then at ambient temperature, followed by evaporation of the THF followed by alternate partitioning between aqueous base and diethyl ether and aqueous acid and diethyl ether, gives I. Separation of I, if desired, may be accomplished by standard techniques. Chromatography on alumina is a convenient technique. For example, IIIa may be treated, in tetrahydrofuran solution, by adding it dropwise to a solution of THF-borane, cooled to about 0° to about 10° C. and maintained at this temperature during the addition period. The reaction mixture may be permitted to warm to ambient temperature, then recooled and treated with an excess of water. After standing for some time at room temperature, conveniently about 60 hours, the tetrahydrofuran may be evaporated and the residue partitioned between diethyl ether and dilute aqueous sodium hydroxide. The organic phase may then be treated with dilute aqueous mineral acid. The aqueous layer may then be made base and partitioned with diethyl ether. The organic phase may then be dried and the solvent evaporated. The residue so obtained may then be chromatographed on grade III alumina to give 2-[(dimethylamino) (3-pyridyl)methyl]cyclohexanol (Ia).

Compounds of formula I wherein R is lower alkanoyl may be prepared by treating the corresponding compound of formula I wherein R is hydrogen with a lower alkyl carboxylic acid anhydride or a lower alkyl carboxylic acid chloride. Compounds of formula I wherein R is lower alkyl may be prepared by treating the corresponding compound of formula I wherein R is hydrogen with a strong base, such as butyl lithium, and a lower alkyl iodide such as methyl iodide.

The compounds of this invention have three assymetric carbon atoms as indicated in the following formula:

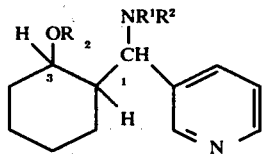

and are capable of existence in eight optically active forms, or four racemic modifications. In the above-described process, all four racemates are observed, but one racemate is the major product when the reduction of the cyclohexanone is performed using borane-THF. If desired, these forms may be separated by known techniques, such as chromatography on silica.

Where used in this specification and claims, the term lower alkyl means straight and branched chain hydrocarbon radicals having from about 1 to about 6 carbon atoms, such as methyl, ethyl, n-propyl, i-propyl and the like. The term lower alkanoyl means lower alkyl carboxyl radicals having from about 2 to about 6 carbon atoms, such as, acetyl, propionyl, 1-methyl-propionyl, and the like.

In practicing the process aspects of inducing analgesia in warm-blooded animals, the compositions can be administered in a variety of dosage forms, either orally or parenterally. The dosage requirements will vary with the particular composition being employed, the severity and nature of the pain, and the animal being treated. With large animals (about 70 kg. body weight), by the oral route, the dose is from about 2 to about 40 mg., and preferably from about 10 to about 25 mg., every four hours, or as needed. By the intramuscular route, the dose is from about 1 to about 20 mg., as needed. Ideally, therapy should be initiated with lower dosages, the dosages thereafter being increased until the desired analgesia is obtained.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant.

The basic compounds of the invention may be used in the form of the free base or in the form of any pharmacologically acceptable acid addition salt thereof. These salts may be simply formed by reaction of the free base form with an equivalent amount of any acid in which the acid addition salt formed would be essentially nontoxic under the conditions of use. Illustrative of these salts are the hydrochloride, hydrobromide, fumarate, maleate, succinate, sulfate, phosphate, tartrate, acetate, citrate, etc. For parenteral administration it is convenient to employ the compounds of the invention in the form of their pharmaceutically acceptable acidaddition salts. These salts are water soluble, and may be readily incorporated into preparations suitable for injection.

The following examples further illustrate the best mode contemplated by the inventor for the practice of his invention.

EXAMPLE 1

2-[(Dimethylamino)(3-Pyridyl)Methyl]-Cyclohexanol Dihydrochloride 2-(3-Pyridylmethylene)cyclohexanone (17.8 g., 7.7 × $10^{-2}$ moles) and dimethylamine (30 ml.) were stored in a pressure bottle during 36 hours. The reaction mixture was evaporated in vacuo, diluted with ether and re-evaporated to remove the last traces of dimethylamine. The residue in THF (40 ml.) was added dropwise, into a stirred 1 molar solution of THF-borane (250 ml., 2.5 × $10^{-1}$ moles) under nitrogen, while maintaining a temperature of 0°–10° C. The reaction mixture was allowed to reach room temperature during 2 hours, recooled to 5° C. and then treated with $H_2O$ (14 ml., 0.75 moles) in THF (200 ml.). The reaction mixture was stored at room temperature during 60 hours. THF was removed in vacuo and the residue distributed between ether and 2N NaOH solution (375 ml.). The ether layer was washed with water and extracted with 1N HCl, vigorous evolution of hydrogen characterized the decomposition of residual amine-boranes. The acid-layer was rebasified strongly with aqueous NaOH and extracted with ether. The organic layer was washed with brine, dried ($Na_2SO_4$) and evaporated to an oil (12.7 g.). Thin layer chromatography on alumina with $CHCl_3$:conc. $NH_4OH$–1:1 (bottom phase) indicated four components, the least polar Rf ca. 0.1 being predominant. Mass spectrum: $M^+234$. Preliminary purification was effected by dry column chromatography on alumina (Woelm, Grade III, neutral 450 g.) developed with $CH_2Cl_2$. 8.5 g. of crude product was obtained and rechromatographed on a Woelm alumina column (240 g., Grade III) built in hexane. Hexane-benzene, benzene, and early benzene-$CH_2Cl_2$ fractions (4:1 through 3:2) eluted less polar components (1.9 g. total). Later benzene-$CH_2Cl_2$ (1:4) and $CHCl_2$-methanol fractions eluted 4.7 g. of the title product as an oil. NMR ($CDCl_3$): δ 2.09 (6H singlet N(C$\underline{H}_3$)$_2$) ppm.

NMR Analysis: signals in CDCl₃ at δ=2.09 (6 proton singlet, N(C*H₃*)₂) ppm.

The oil (4.7 g.) was dissolved in methanol (10 ml.) and treated with 2 equivalents of isopropanolic hydrogen chloride to give the dihydrochloride. The analytical sample was recrystallized from methanol-isopropanol to give 3.54 g. m.p. 261° (decomposition).

Analysis for: $C_{17}H_{26}NO_2Cl \cdot \frac{1}{2} H_2O$;
Calculated: C, 63.62; H, 8.48; N, 4.36; Cl, 11.05;
Found: C, 63.40; H, 8.39; N, 3.80; Cl, 11.08.

EXAMPLE 2

An injectable unit dosage composition is prepared by dissolving 1 g. of 2-[(dimethylamino)(3-pyridyl)methyl]cyclohexanol, hydrochloride in 50 ml. of 0.1 M. phosphate buffer, pH 7.4 and making it up to 100 ml. with distilled water. This solution of medicament, containing 10 mg./ml. of active ingredient is subjected to sterile filtration through a 0.45 micron filter, and 1 ml. aliquots are filled aseptically into sterile ampules. The ampules are flame sealed, and the contents are frozen and stored at −20° C. until needed.

EXAMPLE 3

Tablets for oral use are prepared with the following formulations:

|  | Milligrams | |
|---|---|---|
| 2-[(dimethylamino)(3-pyridyl)methyl]-cyclohexanol | 10 | 15 |
| lactose | 287 | 282 |
| magnesium stearate | 3 | 3 |
|  | 300 | 300 |

EXAMPLE 4

Analgesic acitivity is demonstrated in rats by means of the following procedure, which is a modification of the procedure of D'Amour and Smith, J. Pharmacol., 72, 74 (1941).

Rats weighing approximately 150 to 200 g. are placed in individual holders, and each holder in turn is situated so that a high intensity light beam shines on the tip of the tail. The intensity of the light beam is adjusted so that normal rats respond by moving their tails out of the light beam in 3 to 8 seconds.

The average of 2 readings taken 20 minutes apart serves as a predrug control. Rats are selected for use whose control readings agree within 1 second. Compounds are administered and reaction times are measured every 20 minutes for 2 hours. Analgesic agents cause a significant increase in reaction time.

| Results | | | |
|---|---|---|---|
| Compound | Route | Dose mg/kg. | No. of Rats Showing Analgesia/No. of Rats Tested |
| 2-[(dimethylamino)- | I. P. | 12.50 | 6/6 |
| (3-pyridyl)- | I. P. | 3.12 | 4/10 |
| methyl]cyclohexanol | I. M. | 6.25 | 6/6 |
|  | I. M. | 1.56 | 4/6 |
|  | I. M. | .781 | 0/6 |
|  | P. O. | 3.12 | 6/6 |
|  | P. O. | 1.56 | 2/6 |

EXAMPLE 5

Analgesic acitivity is also demonstrated by means of the following procedure, which is that described by Randall and Selitto, Arch. Int. Pharmacodyn., 111, 409 (1957).

Groups of six male Charles River rats are food deprived for 16 hours prior to testing. Animals are pre-screened for use in the experiments by testing the response of each hind paw to pressure. Only those animals whose readings are within 0.5 weight units are used.

Pressure to the paws of the rats is applied by means of a motor driven screw feed to an adjustable weight which in turn increases the loading of a fulcrum are and pressure stylus. When the rat's foot is placed under the stylus, the drive is started and is stopped when the animal attempts to withdraw his paw. The amount of weight required to elicit the withdrawal is read directly from a graduated scale on the instrument.

Edema is induced by the injection of 0.1 ml. of a 20% yeast-water suspension into the subplantar region of the hind paw. Sixty minutes after the yeast injection, readings are taken on the normal (left hind) paw and on the yeast inflamed (right hind) paw. Test drugs or water controls are then administered orally. Test readings are taken on each paw at one, two, and three hours after drug administration. Responses after dosing are averaged and expressed as the percent increase over control for the normal and the inflamed paw.

| Results | | |
|---|---|---|
| Compound | Dose (mg/kg.) | Response (%) |
| 2-[(dimethylamino)(3-pyridyl)methyl] | 20 | 199 |
| cyclohexanol | 20 | 124 |
|  | 10 | 100 |
|  | 10 | 55 |
|  | 5 | 42 |
|  | 5 | 25 |
|  | 2.50 | 24 |
|  | 2.50 | 11 |

The subject matter which the applicant regards as his invention is particularly pointed out and distinctly claimed as follows:

1. A compound of the formula:

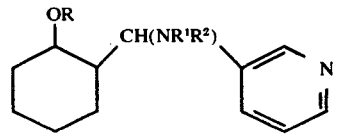

wherein R is hydrogen, lower alkyl, or lower alkanoyl; R¹ is methyl; and R² is methyl, ethyl, or benzyl; or a pharmacologically aceptable acid addition salt thereof.

2. A compound as defined in claim 1 wherein R is hydrogen.

3. A compound as defined in claim 2 wherein R¹ and R² are methyl.

4. A compound as defined in claim 3 wherein the dihydrochloride addition salt thereof has a melting point of 261° C. (with decomposition).

5. A process for producing analgesia in warm-blooded animals which comprises administering to a warm-blooded animal in need thereof an amount sufficient to produce analgesia in said warm-blooded animal of a compound of the formula:

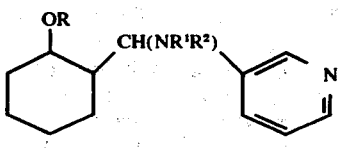

wherein R is hydrogen, lower alkyl, or lower alkanoyl; $R^1$ is methyl; and $R^2$ is methyl, ethyl, or benzyl; or a pharmacologically acceptable acid addition salt thereof.

6. A process as defined in claim 5 wherein R is hydrogen.

7. A process as defined in claim 6 wherein $R^1$ and $R^2$ are methyl.

8. An analgesic composition suitable for administration to a warm-blooded animal comprising:
a. an analgesically effective amount of a compound of the formula:

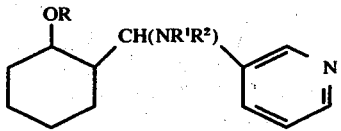

wherein R is hydrogen, lower alkyl, or lower alkanoyl; $R^1$ is methyl; and $R^2$ is methyl, ethyl, or benzyl; or a pharmacologically acceptable acid addition salt thereof.

9. A composition as defined in claim 8 wherein R is hydrogen.

10. A composition as defined in claim 9 wherein $R^1$ and $R^2$ are methyl.

* * * * *